United States Patent [19]

Lagana' et al.

[11] 4,323,252
[45] Apr. 6, 1982

[54] GLAND SEAL SYSTEM FOR USE WITH A METHANATION REACTOR

[75] Inventors: Vincenzo Lagana', Milan; Francesco Saviano, Segrate; Stanislad Ferrantino, San Donato Milanese, all of Italy

[73] Assignee: Snamprogetti S.p.A., Milan, Italy

[21] Appl. No.: 148,193

[22] Filed: May 8, 1980

Related U.S. Application Data

[62] Division of Ser. No. 893,347, Apr. 4, 1978, Pat. No. 4,252,771.

[30] Foreign Application Priority Data

Apr. 15, 1977 [IT] Italy .................. 22499 A/77

[51] Int. Cl.$^3$ .................. F16J 15/14; B01J 8/02; C07C 29/16
[52] U.S. Cl. ............................ 277/12; 277/3; 277/59; 277/135; 277/230; 422/198; 422/208; 422/211; 422/240; 518/728
[58] Field of Search ............ 277/3, 135, 230, 12, 277/59; 422/148, 198, 207, 208, 211, 218, 220, 240, 242; 260/449 M

[56] References Cited

U.S. PATENT DOCUMENTS

| | | | |
|---|---|---|---|
| 1,435,362 | 11/1922 | Wintroath | 277/3 X |
| 1,704,214 | 3/1929 | Richardson | 422/148 X |
| 2,051,774 | 8/1936 | Kleinschmidt | 422/208 |
| 2,109,118 | 2/1938 | Naumann | 422/240 X |
| 2,339,368 | 1/1944 | Bagsar | 422/240 X |
| 2,667,804 | 2/1954 | Boyer et al. | 277/230 X |
| 2,883,214 | 4/1959 | Perlaki | 277/3 |
| 3,041,150 | 6/1962 | Worn | 422/242 X |
| 3,284,163 | 11/1966 | Dear | 277/230 X |
| 3,310,230 | 3/1967 | Wirth | 277/59 X |
| 3,403,915 | 10/1968 | Roberts | 277/59 X |
| 3,440,021 | 4/1969 | Niedetzky et al. | 422/198 X |
| 3,474,734 | 10/1969 | Stogner | 277/59 X |
| 3,477,828 | 11/1969 | Schulze et al. | 422/148 |
| 3,492,099 | 1/1970 | Sze | 422/148 |
| 3,516,800 | 6/1970 | Yamamoto et al. | 422/148 |
| 3,663,179 | 5/1972 | Mehta et al. | 422/148 |
| 3,834,715 | 9/1974 | Butler | 277/59 X |
| 3,994,503 | 11/1976 | Dousse et al. | 277/3 |
| 4,252,771 | 2/1981 | Lagano et al. | 422/198 |

FOREIGN PATENT DOCUMENTS

| | | | |
|---|---|---|---|
| 683417 | 11/1939 | Fed. Rep. of Germany | 277/59 |
| 858261 | 12/1952 | Fed. Rep. of Germany | 277/59 |
| 892743 | 10/1953 | Fed. Rep. of Germany | 422/207 |

*Primary Examiner*—Robert S. Ward, Jr.
*Attorney, Agent, or Firm*—Morgan, Finnegan, Pine, Foley & Lee

[57] ABSTRACT

A methanation reactor to be used preferably in an integrated urea-ammonia process for methanizing carbon oxides is disclosed in which the catalyst bed and an underlying heat exchanger of the tube-bundle type make up a unit mounted centrally of the reactor casing with a gap left between the reactor casing inside wall and centrally mounted unit. Fresh gases to be methanized enter the gap, then into the heat exchanger from below and flow upwards to the catalyst bed and thereafter flow down to the exchanger again. Incoming gases sweep the exchanger tubes from the outside, while the reacted gases flow in the interior of the tubes of the exchanging boundle. Particular blanket and a gland-seal system is provided to minimize the escape of gaseous fluids from the reactor.

1 Claim, 3 Drawing Figures

GLAND SEAL SYSTEM FOR USE WITH A METHANATION REACTOR

This is a division of application Ser. No. 893,347, filed Apr. 4, 1978, now U.S. Pat. No. 4,252,771.

BACKGROUND OF THE INVENTION

This invention relates to a methanation reactor. More particularly, the present invention relates to a methanation reactor which has, inserted therein, a heat exchanger for preheating the cold gases to be sent to the catalytic reaction.

Methanation reactors are known: they are vertical cylindrical holders which contain in their interior one or more layers of a catalyst. Their operation, summarized concisely, is as follow: the hot gases to be methanized enter the reactor at a temperature of about 300° C., flow through the catalyst bed, wherein they are reacted, and exit the reactor at a temperature of about 350° C. The hot gaseous mixture thus obtained is sent to an external heat exchanger so as to preheat to about 300° C. the cold gases to be sent to methanation.

The methanation reactor constructed according to the conventional technology has the disadvantage that it causes the hot gases to be reacted to contact the reactor casing for a certain time and this fact makes it compulsory to work under low pressures or to construct the reactor casing of very expensive types of stainless steels, or to use refractory linings for shielding such casing from the direct contact with the gases. The latter approach involves a further increase in initial costs because, due to the considerable thickness of the linings, the size of the reactors must consequently be enlarged.

It has surprisingly been found, by virtue of the present invention, that the same results can be obtained, from the point of view of the methanized products, by using a reactor having a tube-bundle heat exchanger inserted therein, which is positioned beneath the toroidal catalyst bed, and by adopting a circulation of cold gases to be reacted within the gap between the reactor casing and the catalyst bed-heat exchanger assembly.

SUMMARY OF THE INVENTION

By so doing, the inner walls of the casing and the casing as such are, during the reaction, at a comparatively low temperature and thus they can be constructed with a quite common carbon steel, or, at the most, with a steel having a low precentage of added alloying elements.

This fact permits the ammonia synthesis gases to be methanized with yields which are equal to those of the methods known heretofore, with the undeniable advantage that it becomes possible to use, for the reactor casing, which is subjected to the action of comparatively high pressures, a less sophisticated and thus less expensive material. Especially advantageous, in this respect, are the carbon steels and the steels containing a low percentage of alloying elements, up to 0.5% of molybdenum.

An object of the present invention is to provide a methanation reactor in which the cold gases to reacted enter through the top of the reactor, flow in the gap between the reactor casing and the catalyst bed-heat exchanger assembly, wherein they undergo a slight heating since they must keep the casing cold, rise through the central portion of the reactor and sweep the tubes of the exchanger, (through which the reacted hot gases flow), and are heated until attaining the temperature which is suitable for the reaction. At this stage the preheated gases to be reacted rise through a tube which is coaxial with the catalyst bed and then flow downwardly through the catalyst, wherein they react and are sent into the tubes of the exchanger so as to transfer their reaction heat to the incoming cold gases through the exchanger tube walls. At this stage, the outcoming cooled reactor gases emerge through the reactor bottom wall and are ready for possible subsequent operations.

BRIEF DESCRIPTION OF THE DRAWING

Reference is now to be had to the drawing wherein.

PREFERRED EMBODIMENT OF THE INVENTION

Figure 1:
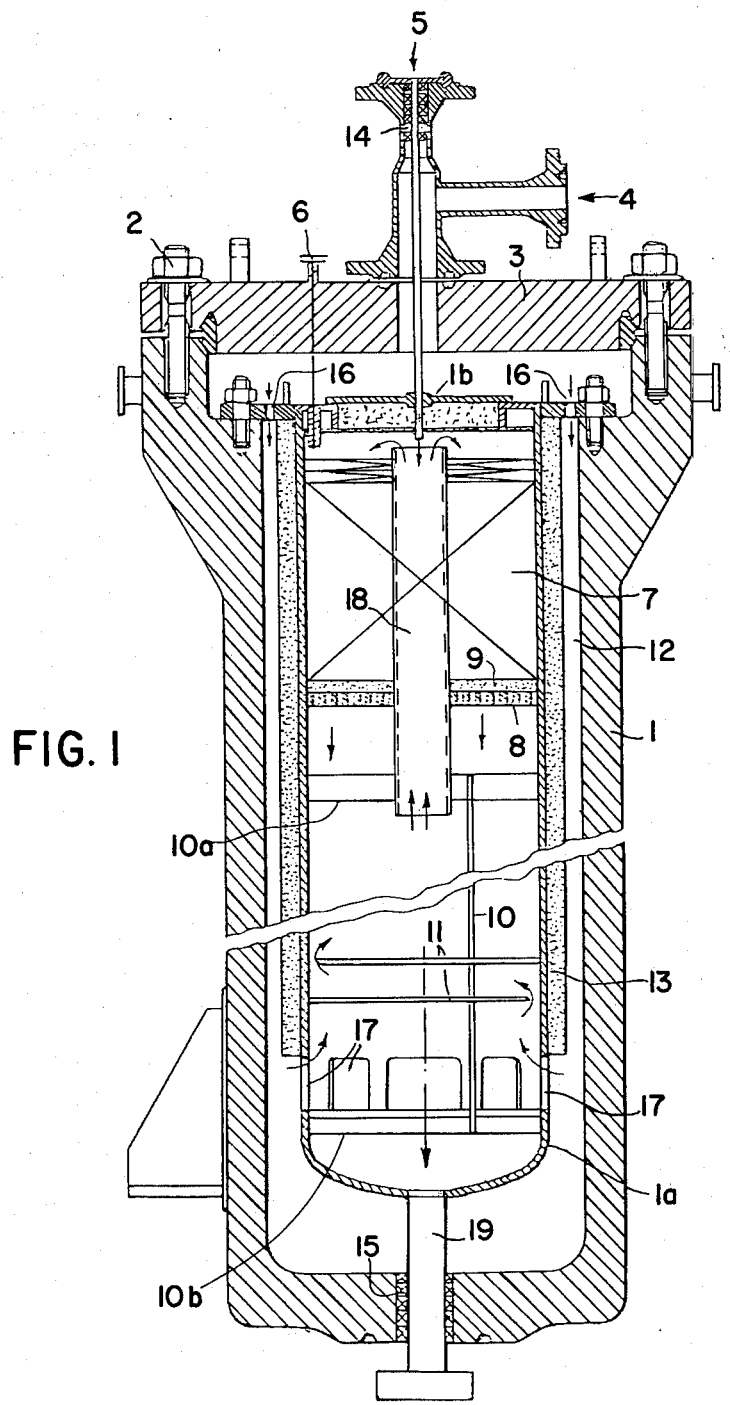
FIG. 1 is a longitudinal cross-sectional view of the reactor made in accordance with the present invention.

The reactor is composed of an outer casing 1 to which the lid 3 is affixed by a set of bolts 2. To the lid 3, in turn, are fastened the tube 4 for introducing the fresh mixture of gases to be reacted during the normal operation run, the tube 5 for introducing the hot gases for starting the reactor operation and the operability of which will be described later, and a well 6, for introducing the thermocouples.

In the interior of the outer casing 1 is mounted an inner casing 1a having cover means in which a toroidal catalyst bed is positioned, indicated at 7, and is supported by a grid 8 and a layer of alumina balls 9, and, beneath the catalyst bed, the tube-bundle heat exchanger 10, of which a single tube only is shown in order not to overcrowd the drawing, is installed: the exchanger is fitted with deflecting baffles 11, in order to improve the heat transfer from the hot gases to the cold one. As illustrated, the single tube shown, of which a plurality thereof will make up the heat exchanger 10, is provided with transversely extending top and bottom tube sheet plates 10a and 10b, respectively, which function to retain the individual tubes of the heat exchanger in place. A central pipe 18 has its lower end extending centrally through the upper sheet plate 10a of the heat exchanger 10. The central pipe 18 extends upwardly and centrally through the support 8 and the catalyst bed 7, with the upper end of the tube extending upward beyond the top of the catalyst bed.

Between the reactor outer casing 1 and the inner casing 1a containing the catalyst bed and the heat exchanger, there is a gap 12. The inner casing is heat-insulated by a layer of insulating material 13, which can be composed by glass-wool, rock-wool or, also, asbestos powder. At the inlet and the outlet of the gases into and from the reactor, there are sennit seals, 14 and 15, to be described in more detail in connection with FIGS. 2 and 3, and the way of operation of which will also be explained hereinafter.

The cold gases enter the methanation reactor through the pipe 4, flow through the gap 12 and via the windows 17 positioned within the inner casing 1a adjacent the lower end thereof and just above the bottom tube sheet 10b, enter the heat exchanger 10 to become heated thereby. The heated gases rise upwardly through the central pipe 18 and then flow downwardly through the interior of the catalyst bed 7. The reacted gases exit from the catalyst bed and then flow downwardly through the exchanger tubes 10 (in their interior), are cooled thereby and exit the methanation reactor through the pipe 19.

Figure 2:
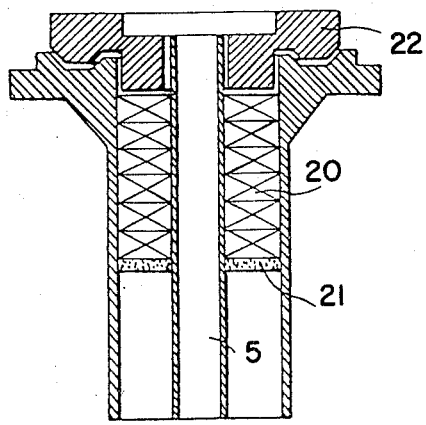
FIG. 2 is an enlarged fragmentary cross-sectional view of the sennit seal system made in accordance with the present invention.

When the reactor is started, or restarted in the cold, it is necessary that a certain amount of hot gases to be reacted be fed, heated to the reaction temperature, and thus such gases can be introduced through the duct 4 to avoid heating the casing walls. To prevent this, the reacting hot gases are fed directly to the catalyst via the duct 5, whereas the cold gases are fed through the duct 4, as before. To prevent the admixture of the hot gases with the cold ones, the sennit seal system 14 has been adopted, which is best seen in FIG. 2. The seal system comprises the sennit braids 20, the abutments 21 and the packing gland 22 which urges the sennit against the abutments, so providing a tight seal for the cold gases. Another sealing problem is present at the bottom of the methanation reactor where, due to downward expansion of the duct 19, there can be leaks of reacting gases in the area of contact between the duct and the casing walls.

To solve this problem, a gland seal system is adopted which is equipped with an intermediate hollow bushing and permits the forced circulation of water under pressure to prevent dangerous processing gases from escaping the reactor.

Figure 3:
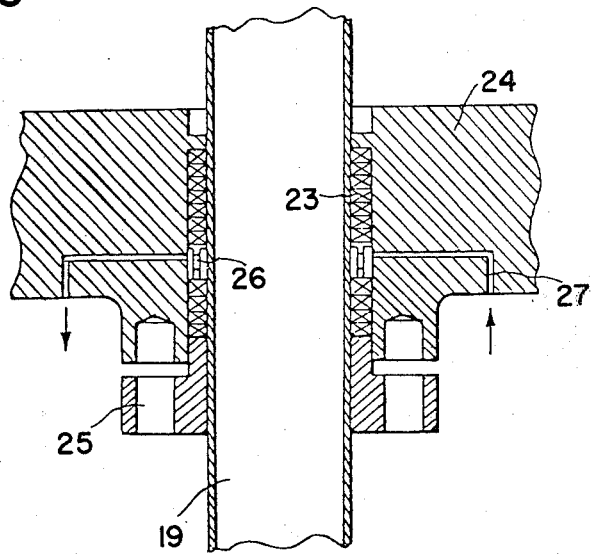
FIG. 3 is an enlarged fragmentary cross-sectional view of a gland sealing system made in accordance with the present invention.

FIG. 3 is a diagrammatical showing of this particular kind of seal. Between the outside wall of the duct 19 and the casing 1 there is arranged an asbestos braid 23 (sennit) which is kept pressed in position by the reactor bottom wall 24 and by a flanged gland 25. The sennit is divided into two slugs by a bushing 26: the latter is connected via a channel 27 to a source of water under pressure. Whenever a leak occurs in the seal system, the reacting gases cannot exit the reactor since water enters the reactor under a pressure which exceeds the pressure existing in the reactor.

The kind of methanation reactor as described in the foregoing is particularly advantageous in the integrated ammonia-urea plants since it permits the methanation of $CO_2$ and CO under the same pressure existing in the ammonia reactor. Thus, the necessity of compressing the methanized gaseous mixture up to the pressure of the synthesis is eliminated which is no little advantage.

We claim:

1. In a methanation reactor having a reactor casing, an opening at one end of said casing, a discharge tube positioned within said opening for passing reacted gases from the interior of the reactor casing to the exterior thereof and seal means for sealing said tube at its point of passage through said reactor opening, the improvement of seal means comprising upper sealing means positioned in encircled relationship around the discharge tube at the exit point of said tube through the opening in said casing to form a tight seal between the opening and the tube, lower sealing means encircling said discharge tube in spaced relationship from said upper sealing means, bushing means in encircling relationship around said tube and positioned between said upper and lower sealing means, said bushing means having channel means formed therein through which water can enter and thereafter pass through and exit from said bushing means at a pressure greater than the internal pressure within the reactor casing and means for maintaining said upper and lower sealing means and said bushing means in a compressed state between the reactor casing opening and the discharge tube.

* * * * *